US00PP25408P3

(12) United States Plant Patent
Vitten et al.

(10) Patent No.: US PP25,408 P3
(45) Date of Patent: Apr. 7, 2015

(54) STRAWBERRY PLANT NAMED 'DRISSTRAWTHIRTYNINE'

(50) Latin Name: *Fragaria×ananassa*
Varietal Denomination: DrisStrawThirtyNine

(71) Applicant: Driscoll Strawberry Associates, Inc., Watsonville, CA (US)

(72) Inventors: Matthias D. Vitten, Aptos, CA (US); Carlos D. Fear, West Malling (GB); Abigail Johnson, Rochester (GB)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 166 days.

(21) Appl. No.: 13/815,232

(22) Filed: Feb. 12, 2013

(65) Prior Publication Data

US 2014/0230113 P1 Aug. 14, 2014

(51) Int. Cl.
*A01H 5/00* (2006.01)

(52) U.S. Cl.
USPC ..... Plt./209

(58) Field of Classification Search
USPC ..... Plt./209
See application file for complete search history.

*Primary Examiner* — Anne Grunberg
(74) *Attorney, Agent, or Firm* — Jondle & Associates, P.C.

(57) ABSTRACT

A new and distinct variety of strawberry plant named 'DrisStrawThirtyNine' particularly characterized by a fully everbearing plant having conic shaped fruit and resistance to *Verticillium* wilt is disclosed.

3 Drawing Sheets

Genus and species: *Fragaria×ananassa.*
Variety denomination: 'DrisStrawThirtyNine'.

BACKGROUND OF THE NEW PLANT

The present invention relates to a new and distinct strawberry variety designated 'DrisStrawThirtyNine' and botanically known as *Fragaria×ananassa*. This new strawberry variety was discovered in Kent, United Kingdom in August 2007 and originated from a cross between the proprietary female parent 'Ophelia' (unpatented) and the proprietary male parent 'KGEM 93' (unpatented). A single plant was selected and asexually propagated via tissue culture and vegetative cuttings in Kent, United Kingdom in 2007.

'DrisStrawThirtyNine' underwent further testing in Kent, United Kingdom for six years (2007-2012). The present invention has been found to retain its distinctive characteristics through successive asexual propagations via stolons and tissue culture.

Plant Breeder's Rights for this variety have not been applied for. 'DrisStrawThirtyNine' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Kent, United Kingdom.

1. Fully everbearing plant;
2. Conic shaped fruit; and
3. Resistance to *Verticillium* wilt.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from five to six-month-old plants.

DESCRIPTION OF THE NEW VARIETY

Figure 1:
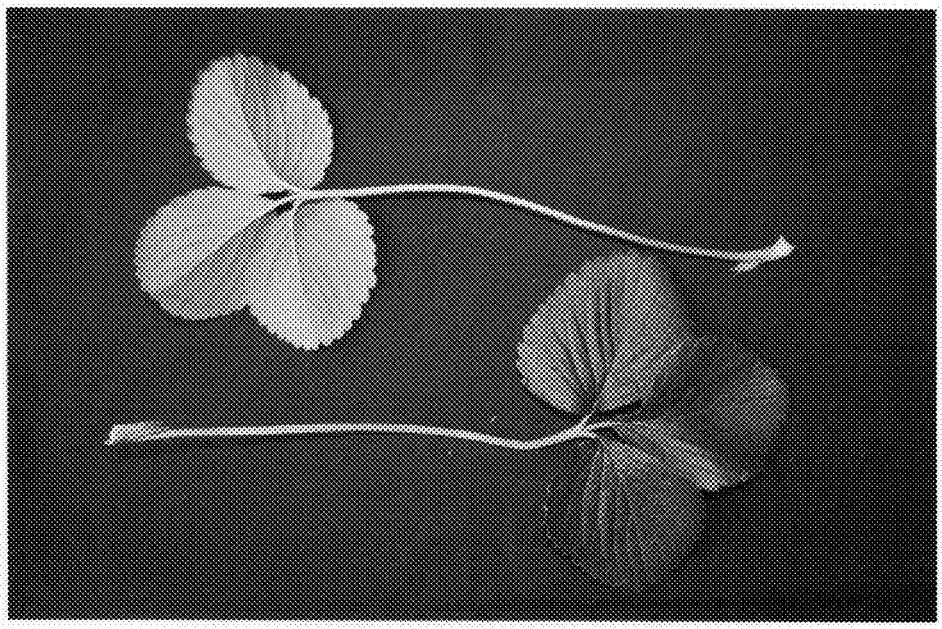
FIG. 1 shows upper and lower surfaces of the leaves of the plant with three leaflets.
Figure 2:
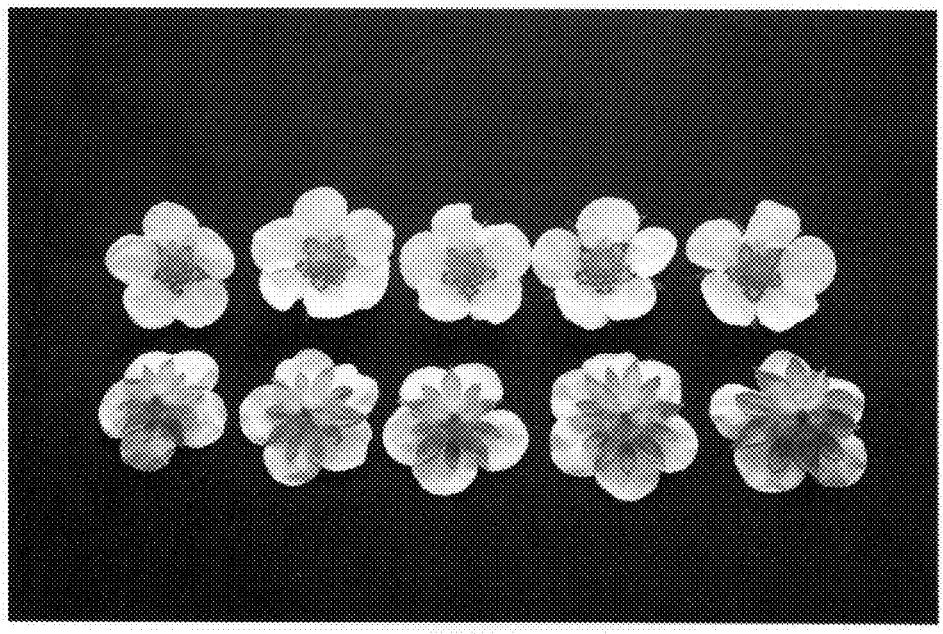
FIG. 2 shows both upper and lower surfaces of the flowers.
Figure 3:
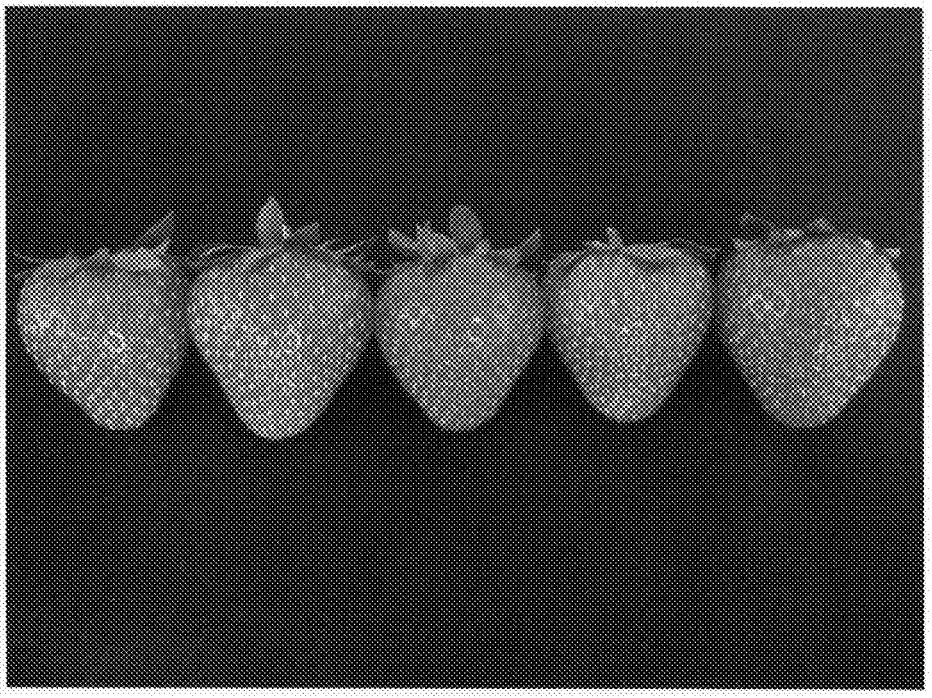
FIG. 3 shows the whole fruit.
Figure 4:
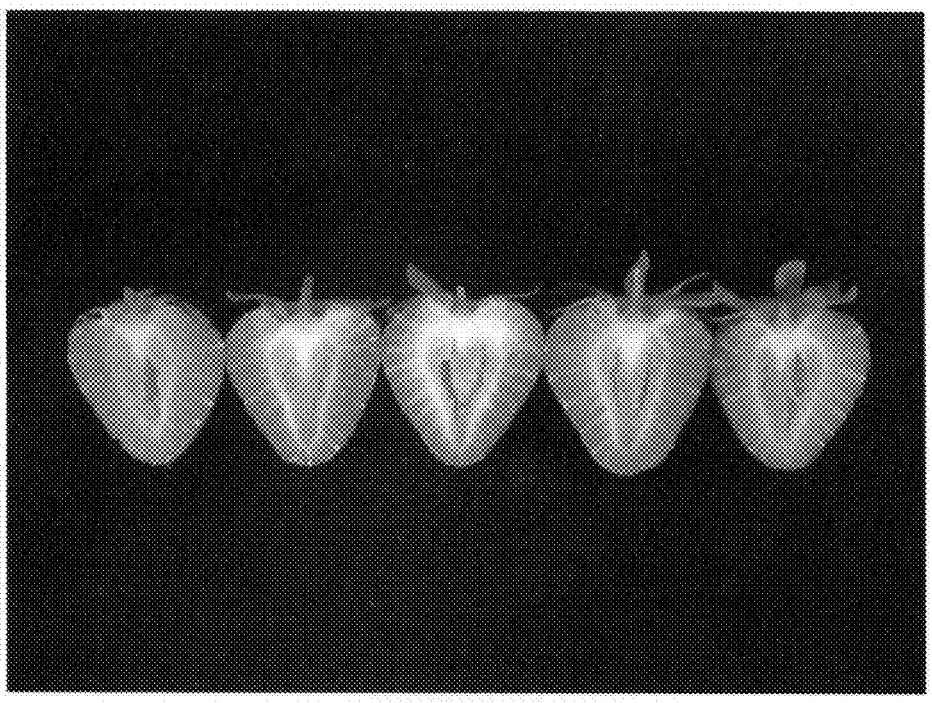
FIG. 4 shows the fruit in longitudinal cross-section.
Figure 5:
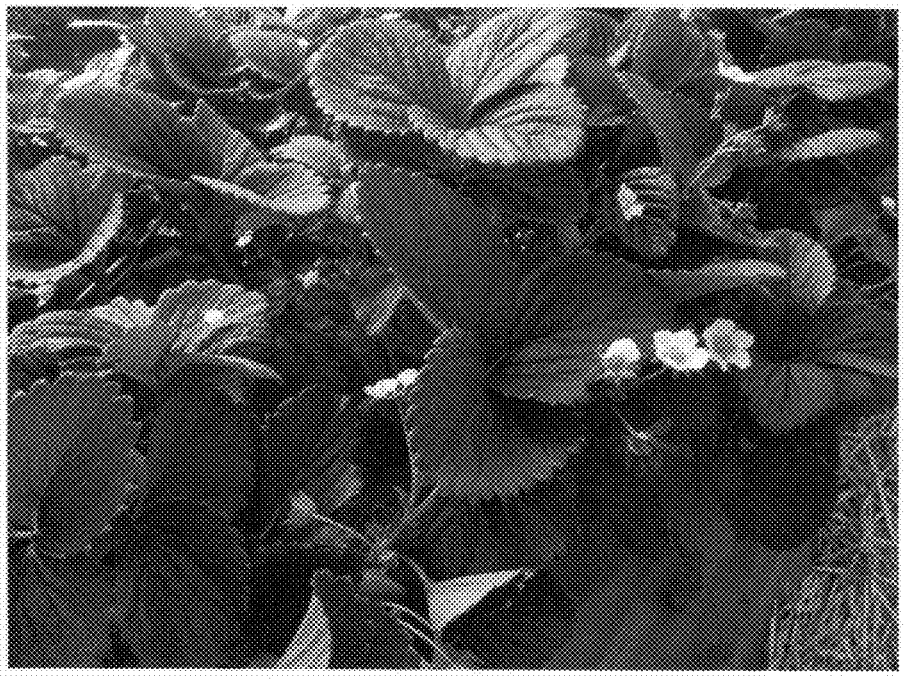
FIG. 5 shows the whole plant.

The following detailed descriptions set forth the distinctive characteristics of 'DrisStrawThirtyNine'. The data which define these characteristics is based on observations taken in Kent, United Kingdom from 2007 to 2012. This description is in accordance with UPOV terminology. Color designations, color descriptions, and other phenotypical descriptions may deviate from the stated values and descriptions depending upon variation in environmental, seasonal, climatic, and cultural conditions. 'DrisStrawThirtyNine' has not been observed under all possible environmental conditions. The botanical description of 'DrisStrawThirtyNine' was taken from five to six-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:

*Species.*—*Fragaria×ananassa.*
*Common name.*—Strawberry.
*Denomination.*—'DrisStrawThirtyNine'.

Parentage:
*Female parent*.—The proprietary variety 'Ophelia' (unpatented).
*Male parent*.—The proprietary variety 'KGEM 93' (unpatented).

Plant:
*Height*.—40.8 cm.
*Diameter*.—58.7 cm.
*Number of crowns/plant*.—3.
*Habit*.—Globose — semi-upright.
*Density of individual plant*.—Medium.
*Vigor* (*health and hardiness of plant*).—Medium.

Terminal leaflets:
*Size*.—Medium. Length: 9.56 cm. Width: 8.39 cm. Length/width ratio: 1.1 (Longer than broad).
*Number of teeth/terminal leaflet*.—25.
*Shape of teeth*.—Obtuse — serrate to crenate.
*Color*.—Upper surface: RHS N137B (Medium green). Lower surface: RHS 137C (Medium green).
*Shape in cross section*.—Flat — straight.
*Blistering*.—Medium.
*Glossiness*.—Medium.
*Number of leaflets*.—Three only.
*Shape*.—Oval.
*Base shape*.—Obtuse.
*Apex descriptor*.—Convex.
*Variegation*.—Absent.
*Margin*.—Entire.
*Margin profile*.—Revolute.

Petiole:
*Length*.—Medium; 23.7 mm.
*Diameter*.—4.83 mm.
*Pubescence*.—Absent or very sparse.
*Pose of hairs*.—Slightly upwards.
*Color*.—RHS 144B (Medium yellow-green).
*Bract frequency*.—0.

Petiolule:
*Length*.—14.82 mm.
*Diameter*.—2.84 mm.
*Color*.—RHS 144C (Medium yellow-green).

Stipule:
*Length*.—3.2 cm.
*Width*.—10.75 mm.
*Pubescence*.—Medium.
*Stipule anthocyanin coloration*.—Medium; RHS 47C (Medium red).

Stolon:
*Number*.—Many.
*Average number of daughter plants per square foot*.—7.
*Stolon anthocyanin*.—Absent or very weak; RHS 144B (Medium yellow-green).
*Diameter at bract*.—4.10 mm.
*Thickness*.—Medium.
*Pubescence*.—Medium.

Inflorescence:
*Position relative to foliage*.—Beneath.
*Number of flowers*.—Medium.
*Time of flowering* (*50% of plants at first flower*).—Medium; July $10^{th}$-August $1^{st}$.
*Flower size*.—Medium.
*Diameter*.—28.91 mm.
*Petals*.—Shape: Orbicular. Apex: Rounded. Base: Concavo-convex. Margin: Entire. Spacing: Overlapping. Length: 12.96 mm. Width: 12.87 mm. Length/width ratio: 1.0 (As long as broad). Petal number per flower: 5. Color (upper surface): RHS 155B (White).
*Calyx*.—Diameter: 24.63 mm. Diameter relative to corolla: Smaller. Inner calyx diameter relative to outer: Same size. Insertion of calyx: Level. Pose of calyx segments: Spreading to outwards. Size of calyx in relation to fruit: Same size. Adherence of calyx: Medium.
*Sepal*.—Shape: Elliptical. Apex: Convex. Margin: Entire. Length: 9.24 mm. Width: 4.95 mm. Sepal number: 10.
*Receptacle color*.—RHS 151B (Medium yellow-green).
*Stamen*.—Present. Anther color: RHS 153D (Medium yellow-green).
*Pedicel*.—Attitude of hairs: Upwards.

Fruiting truss:
*Length*.—Medium; 37.4 cm.
*Diameter at base of truss*.—4.9 mm.
*Number of berries per fruiting truss*.—13.
*Attitude at first picking*.—Semi-erect.
*Color at base of truss*.—RHS 144B (Medium yellow-green).

Fruit:
*Relative fruit size*.—Medium.
*Length*.—36.24 mm.
*Width*.—36.46 mm.
*Length/width ratio*.—1.0 (As long as broad).
*Fruit hollow length*.—26.70 mm.
*Fruit hollow width*.—15.15 mm.
*Fruit hollow length/width ratio*.—1.8 (Much longer than broad).
*Fruit hollow center* (*cavity*).—Small.
*Weight* (*per individual berry*).—18.1 g.
*Predominant fruit shape*.—Conical.
*Difference in shape between primary and secondary fruits*.—None or very slight.
*Evenness of fruit surface*.—Even or very slightly uneven.
*Fruit skin color*.—RHS 45A (Medium red).
*Evenness of fruit color*.—Even or very slightly uneven.
*Fruit glossiness*.—Medium.
*Achenes*.—Insertion of achenes: Level with surface. Coloration (sunward side of berry): RHS N170B (Medium greyed-orange). Coloration (shaded side of berry): RHS N170B (Medium greyed-orange). Number per berry: 296. Weight (weight of achenes divided by total # seed): 0.6 mg. Width of band without achenes: Narrow.
*Firmness of flesh* (*when fully ripe*).—Medium.
*Color of flesh* (*excluding core*).—RHS 40A (Medium red).
*Color of core*.—RHS 40C (Light red).
*Evenness of flesh color*.—Even.
*Distribution of flesh color*.—Marginal and central.
*Sweetness*.—Medium; average 8.5° Brix.
*Acidity*.—Weak.
*Texture when tasted*.—Fine.
*Type of bearing*.—Fully everbearing — fully remontant.
*Grams of fruit/plant*.—1200.0 g.
*Harvest interval*.—Late June — early October.
*Harvest maturity*.—Mid-season.

Disease and pest resistance:

*Botrytis fruit rot*.—Moderately resistant.

*Powdery mildew*.—Moderately resistant.

*Verticillium wilt*.—Resistant.

COMPARISON WITH PARENTAL AND COMMERCIAL VARIETIES

When 'DrisStrawThirtyNine' is compared to the female parent 'Ophelia' (unpatented), 'DrisStrawThirtyNine' has higher yields, a higher percentage of Class 1 fruit, and better flavor and shelf life than 'Ophelia'.

When 'DrisStrawThirtyNine' is compared to the male parent 'KGEM 93' (unpatented), 'DrisStrawThirtyNine' is fully everbearing, whereas 'KGEM 93' is not everbearing.

When 'DrisStrawThirtyNine' is compared to the commercial variety 'DrisStrawTwo' (U.S. Plant Pat. No. 18,878), 'DrisStrawThirtyNine' has a globose habit, medium leaf blistering, an obtuse terminal leaflet base, and inflorescence positioned beneath the foliage, whereas 'DrisStrawTwo' has a flat globose habit, strong leaf blistering, a rounded terminal leaflet base, and inflorescence positioned above the foliage. Additionally, 'DrisStrawThirtyNine' has fruit with medium glossiness and a narrow band without achenes, whereas 'DrisStrawTwo' has fruit that is strongly glossy with a medium band without achenes.

When 'DrisStrawThirtyNine' is compared to the commercial variety 'Driscoll Camarillo' (U.S. Plant Pat. No. 14,771), 'DrisStrawThirtyNine' has leaves that are flat in cross section with medium blistering, an obtuse base and inflorescence positioned beneath the foliage, whereas 'Driscoll Camarillo' has leaves that are concave in cross section with very strong blistering, a rounded base and inflorescence positioned above the foliage. Additionally, 'DrisStrawThirtyNine' has conical shaped fruit with medium glossiness, whereas 'Driscoll Camarillo' has cordate shaped fruit that is strongly glossy.

We claim:

1. A new and distinct variety of strawberry plant named 'DrisStrawThirtyNine' as described and illustrated herein.

* * * * *